US 11,242,307 B1

(12) United States Patent
Zhang et al.

(10) Patent No.: US 11,242,307 B1
(45) Date of Patent: Feb. 8, 2022

(54) METHOD FOR PREPARING ALKYNYL 2-HALO-2,2-DIFLUOROACETATE

(71) Applicants: Hangzhou Transfar Fine Chemical Co., Ltd., Zhejiang Province (CN); Hangzhou Normal University, Hangzhou (CN); Zhejiang Transfar Functional New Material Co., Ltd., Hangzhou (CN)

(72) Inventors: Pengfei Zhang, Hangzhou (CN); Shengpeng Wang, Hangzhou (CN); Wanmei Li, Hangzhou (CN); Weiming Xu, Hangzhou (CN); Bajin Chen, Hangzhou (CN); Xiaojun Wang, Hangzhou (CN)

(73) Assignees: Hangzhou Transfar Fine Chemical Co., Ltd., Zhejiang Province (CN); Hangzhou Normal University, Hangzhou (CN); Zhejiang Transfar Functional New Material Co., Ltd., Hangzhou (CN)

( * ) Notice: Subject to any disclaimer, the term of this patent is extended or adjusted under 35 U.S.C. 154(b) by 0 days.

(21) Appl. No.: 17/061,028

(22) Filed: Oct. 1, 2020

(30) Foreign Application Priority Data

Jul. 28, 2020 (CN) .......................... 202010735944.9

(51) Int. Cl.
*C07C 67/08* (2006.01)
*C07C 69/63* (2006.01)

(52) U.S. Cl.
CPC .............. *C07C 67/08* (2013.01); *C07C 69/63* (2013.01)

(58) Field of Classification Search
None
See application file for complete search history.

(56) References Cited

U.S. PATENT DOCUMENTS

2020/0052322 A1* 2/2020 Yu ....................... H01M 10/052

FOREIGN PATENT DOCUMENTS

CN 111362801 * 7/2020

OTHER PUBLICATIONS

Yang ("Synthesis of 2', 3'-Dideoxy-6',6'-difluorocarbocyclic Nucleosides" Org. Lett. 2004, 6(23), p. 4257-4259, including Supporting Information p. S1-S15). (Year: 2004).*
Pubchem record for sulfuric acid: https://pubchem.ncbi.nlm.nih.gOv/compound/1118#section=Density&fullscreen=true, downloaded on Jun. 24, 2021 (Year: 2021).*
Pubchem record for toluene: https://pubchem.ncbi.nlm.nih.gov/compound/Toluene#section=Density&fullscreen=true, downloaded on Jun. 24, 2021 (Year: 2021).*

* cited by examiner

*Primary Examiner* — Amy C Bonaparte
(74) *Attorney, Agent, or Firm* — Hickman Becker Bingham Ledesma LLP

(57) ABSTRACT

A method for preparing alkynyl 2-halo-2,2-difluoroacetate is disclosed. The method comprises: subjecting a 2-halo-2,2-difluoro acetic acid, an alkynol, and a catalyst to an esterification reaction in a solvent, to obtain alkynyl 2-halo-2,2-difluoroacetate, wherein the catalyst includes one or more of sulfuric acid, phosphoric acid and p-toluenesulfonic acid.

5 Claims, 3 Drawing Sheets

METHOD FOR PREPARING ALKYNYL 2-HALO-2,2-DIFLUOROACETATE

RELATED APPLICATION

This application claims priority under 35 U.S.C. 119(a)-(d) to Foreign Application No. 202010735944. 9 filed in China entitled "Method for Preparing Alkynyl 2-Halo-2,2-Difluoroacetate" and filed on Jul. 28, 2020, the contents of which are herein incorporated in their entirety by reference for all purposes.

TECHNICAL FIELD

The present disclosure relates to a technical field of organic synthesis, and particularly to a method for preparing alkynyl 2-halo-2,2-difluoroacetate.

BACKGROUND

The polymer additives, water-borne polyacrylate (PA) generally have defects such as easy absorbtion of moisture and poor weather resistance. In order to improve the above-mentioned problems of polyacrylate, people generally make improvements and modifications to the structure of polyacrylate.

Modified monomer is not only required to have a novel structure, but also required to be easy to copolymerize. The substituent of C2 is designed as two fluorine atoms and one bromine atom or chlorine atom, so that the modified monomer has a certain degree of hydrophobicity, and meanwhile it imparts improved moisture-proof and flame-retardant properties to the additive. In addition, the modified monomer is designed to contain an alkynyl group, and it is conducive to allowing the modified monomer to participate in the polymerization reaction, thereby realizing the modification of the material. Therefore, 2-halo-2,2-difluoroacetate is an ideal monomer for modified polyacrylate. However, there is no relevant report on the preparation method of 2-halo-2,2-difluoroacetin in the prior art.

SUMMARY

A method is provided in this disclosure for preparing alkynyl 2-halo-2,2-difluoroacetate. Alkynyl 2-halo-2,2-difluoroacetate prepared by the method provided by the present disclosure has the advantages of a high product yield, and a high purity.

The present disclosure provides a method for preparing alkynyl 2-halo-2,2-difluoroacetate, comprising the following steps:
subjecting a 2-halo-2,2-difluoro acetic acid, an alkynol, and a catalyst to an esterification reaction in a solvent, to obtain alkynyl 2-halo-2,2-difluoroacetate, wherein the catalyst includes one or more of sulfuric acid, phosphoric acid and p-toluenesulfonic acid.

In some embodiments, the 2-halo-2,2-difluoro acetic acid is 2-bromo-2,2-difluoroacetic acid and/or 2-chloro-2,2-difluoroacetic acid.

In some embodiments, the esterification reaction is carried out under reflux condition, wherein during the esterification reaction, the water produced by the esterification reaction is continuously separated.

In some embodiments, the esterification reaction is carried out at a temperature of 60-130° C. for 5-15 hours.

In some embodiments, the alkynol includes one or more of propargyl alcohol, 3-butyn-1-ol, 4-pentyn-1-ol and 5-hexyn-1-ol.

In some embodiments, a molar ratio of the 2-halo-2,2-difluoro acetic acid to the alkynol is 1:1-5.

In some embodiments, a mass ratio of the 2-halo-2,2-difluoro acetic acid to the catalyst is 1:0.01-0.1.

In some embodiments, the solvent includes one or more of cyclohexane, toluene and xylene.

In some embodiments, a mass ratio of the 2-halo-2,2-difluoro acetic acid to the solvent is 1:4-10.

Beneficial Effects

The present disclosure provides a method for preparing alkynyl 2-halo-2,2-difluoroacetate, comprising: subjecting a 2-halo-2,2-difluoro acetic acid, an alkynol, and a catalyst to an esterification reaction in a solvent, to obtain alkynyl 2-halo-2,2-difluoroacetate, wherein the catalyst includes one or more of sulfuric acid, phosphoric acid and p-toluenesulfonic acid. Alkynyl 2-halo-2,2-difluoroacetate could be prepared by the method provided by the present disclosure, and the method is simple for operation and environmentally friendly, and could achieve a high product yield. Results of the examples show that the method for preparing alkynyl 2-halo-2,2-difluoroacetate provided by the present disclosure has a yield of 95.0%-98.8%.

DETAILED DESCRIPTION OF THE EMBODIMENTS

Figure 1:
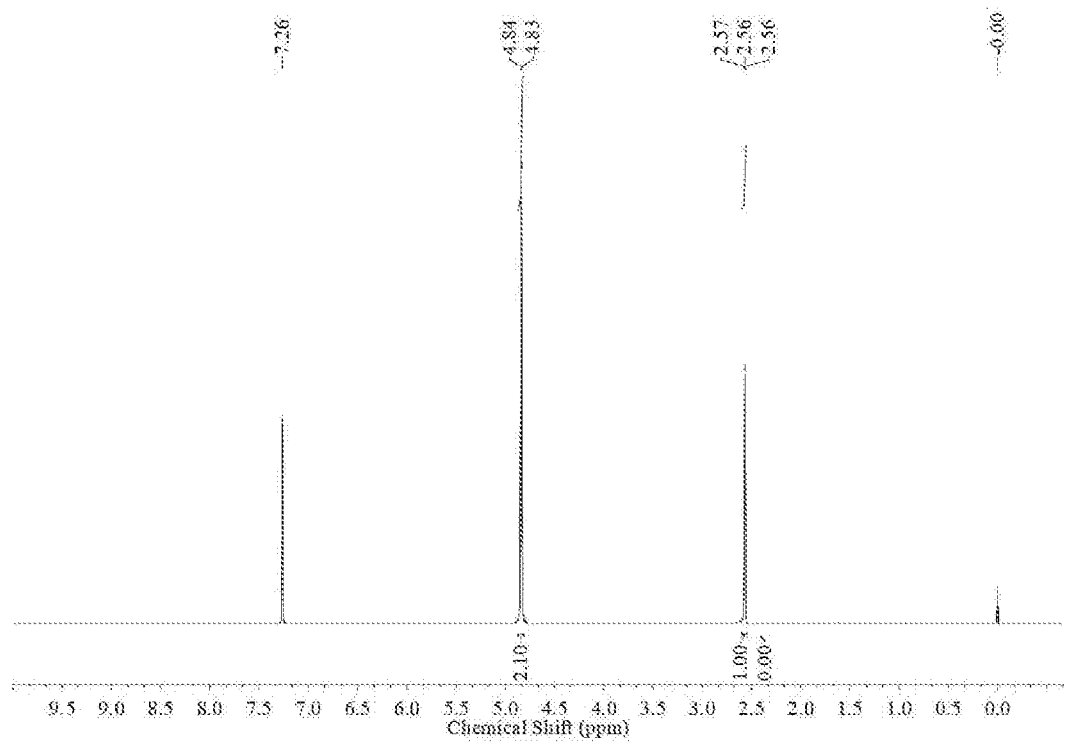
FIG. 1 illustrates a hydrogen nuclear magnetic resonance ($^1$H-NMR) spectrum of propargyl 2-bromo-2,2-difluoroacetate as prepared in Example 1.

The present disclosure provides a method for preparing alkynyl 2-halo-2,2-difluoroacetate, comprising the following steps:
subjecting a 2-halo-2,2-difluoro acetic acid, an alkynol, and a catalyst to an esterification reaction in a solvent, to obtain alkynyl 2-halo-2,2-difluoroacetate, wherein the catalyst includes one or more of sulfuric acid, phosphoric acid and p-toluenesulfonic acid.

In the present disclosure, the 2-halo-2,2-difluoro acetic acid, the alkynol, and the catalyst are mixed in the solvent. In some embodiments of the present disclosure, the 2-halo-2,2-difluoro acetic acid is 2-bromo-2,2-difluoroacetic acid and/or 2-chloro-2,2-difluoroacetic acid. In some embodiments of the present disclosure, the alkynol includes one or more of propargyl alcohol, 3-butyn-1-ol, 4-pentyn-1-ol and 5-hexyn-1-ol. In some embodiments of the present disclosure, the solvent includes one or more of cyclohexane, toluene and xylene.

In some embodiments of the present disclosure, a molar ratio of the 2-halo-2,2-difluoro acetic acid to the alkynol is 1:1-5. In some other embodiments, a molar ratio of the 2-halo-2,2-difluoro acetic acid to the alkynol is 1:1, 1:2, 1:3, 1:4, or 1:5. In some embodiments of the present disclosure, a mass ratio of the 2-halo-2,2-difluoro acetic acid to the catalyst is 1:0.01-0.1. In some other embodiments, a mass ratio of the 2-halo-2,2-difluoro acetic acid to the catalyst is 1:0.01, 1:0.02, 1:0.03, 1:0.04, 1:0.05, 1:0.06, 1:0.07, 1:0.08, 1:0.09 or 1:0.1. In some embodiments of the present disclosure, a mass ratio of the 2-halo-2,2-difluoro acetic acid to the solvent is 1:4-10. In some other embodiments, a mass ratio of the 2-halo-2,2-difluoro acetic acid to the solvent is 1:4, 1:5, 1:6, 1:7, 1:8, 1:9 or 1:10.

In some embodiments of the present disclosure, the esterification reaction is carried out at a temperature of 60-130° C. In some other embodiments, the esterification reaction is carried out at a temperature of 60° C., 70° C., 80° C., 90° C., 100° C., 110° C., 120° C. or 130° C. In the present disclosure, during the esterification reaction, the water produced by the esterification reaction is continuously separated. In some embodiments of the present disclosure, a water separator is configured in the device where the esterification reaction is carried out, and water in the reaction system is removed by the reflux of the reaction system, so as to achieve the purpose of improving the reaction yield and product purity.

The esterification reaction is stopped when no water is separated from the reaction system. In some embodiments of the present disclosure, the esterification reaction is carried out for 5-15 hours. In some other embodiments, the esterification reaction is carried out for 5 hours, 6 hours, 7 hours, 8 hours, 9 hours, 10 hours, 11 hours, 12 hours, 13 hours, 14 hours or 15 hours.

In the present disclosure, an equation of the esterification reaction is shown in Formula (1) or Formula (2):

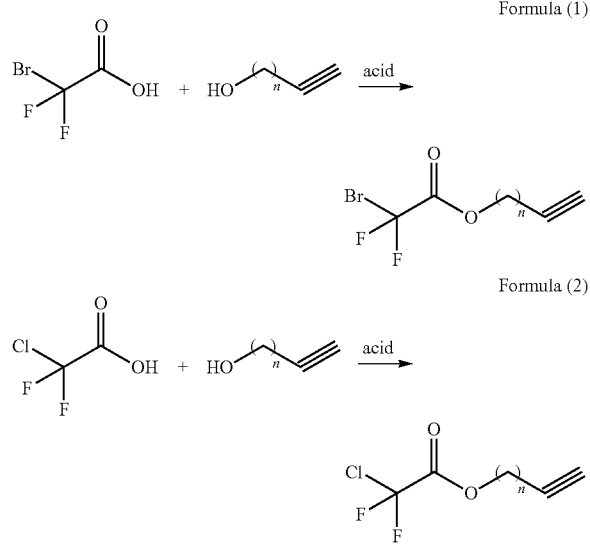

In the present disclosure, types of raw materials, the amount of the raw materials, and reaction conditions of the esterification reaction are controlled within the scope above, to help to improve the yield and product purity.

After the esterification reaction is completed, in some embodiments of the present disclosure, the esterification reaction system is subjected to a distillation treatment to recover the solvent and excess alkynol, then the remaining substances after the distillation treatment are subjected to a distillation under reduced pressure, and the fractions are collected, to obtain alkynyl 2-halo-2,2-difluoroacetate.

Details of the embodiments are described below in reference with several examples.

Example 1

In one embodiment, 87.5 grams of 2-bromo-2,2-difluoroacetic acid, 140 grams of propargyl alcohol, 8.75 grams of phosphoric acid and 350 grams of cyclohexane were added into a reactor equipped with a thermometer, a reflux condenser, a water separator and a stirrer, and were subjected to a reaction at 70° C. until that no water was separated, and the reaction was carried out for 15 hours. After the reaction was completed, a distillation treatment was performed to recover the solvent and excess alkynol, then the remaining substances were subjected to a distillation under reduced pressure, and the fractions under the condition of 115-117° C./50 mmHg were collected, to obtain 104.8 grams of propargyl 2-bromo-2,2-difluoroacetate with a yield of 98.4%, and a purity of 99.4%.

Figure 2:
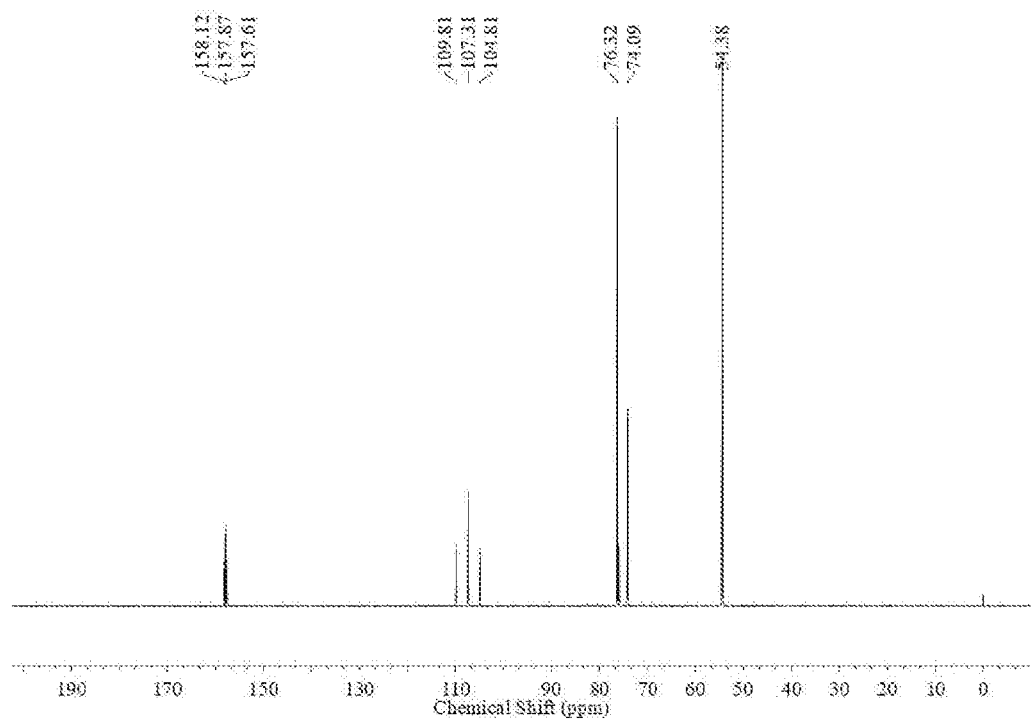
FIG. 2 illustrates a carbon nuclear magnetic resonance ($^{13}$C-NMR) spectrum of propargyl 2-bromo-2,2-difluoroacetate as prepared in Example 1.
Figure 3:
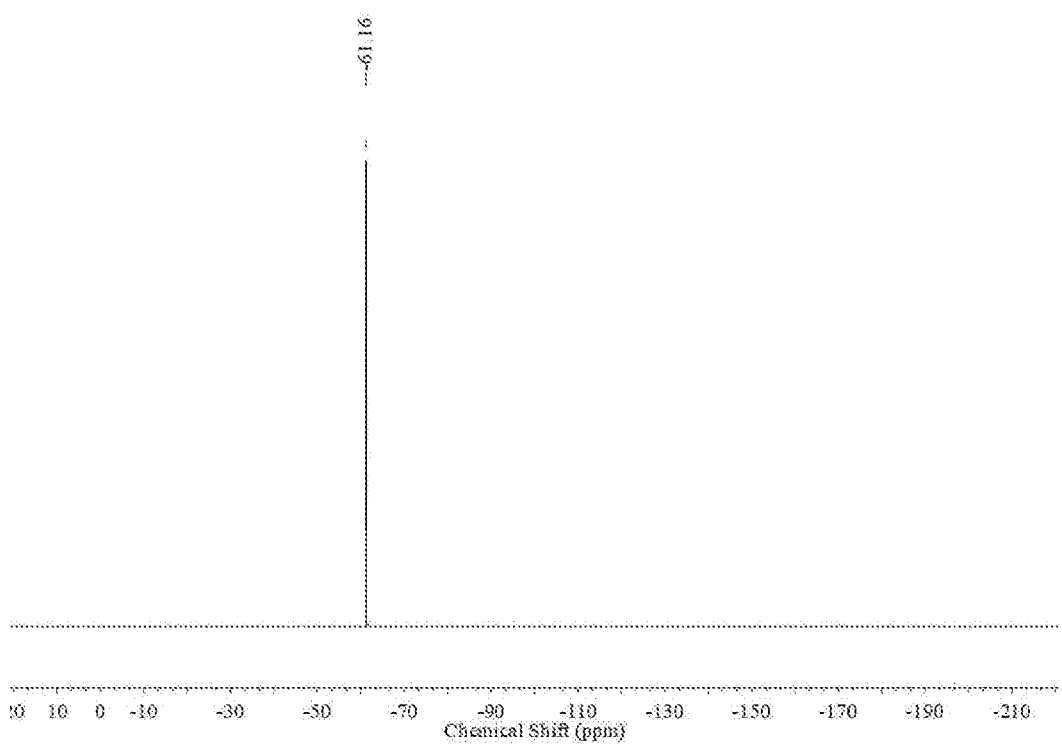
FIG. 3 illustrates a fluorine nuclear magnetic resonance ($^{19}$F-NMR) spectrum of propargyl 2-bromo-2,2-difluoroacetate as prepared in Example 1.

Propargyl 2-bromo-2,2-difluoroacetate prepared in Example 1 was subjected to a nuclear magnetic resonance analysis. The results were shown in FIGS. 1-3, wherein FIG. 1 illustrates a hydrogen nuclear magnetic resonance spectrum and FIG. 2 illustrates a carbon nuclear magnetic resonance spectrum, and FIG. 3 illustrates a fluorine nuclear magnetic resonance spectrum. As can be seen from FIGS. 1-3, the structure of propargyl 2-bromo-2,2-difluoroacetate prepared in Example 1 was confirmed by the nuclear magnetic resonance analysis.

Data shown in the hydrogen nuclear magnetic resonance spectrum of FIG. 1 was as follows: $^1$H-NMR (500 MHz, CDCl$_3$) δ 4.84 (d, J=2.5 Hz, 2H), 2.56 (t, J=2.2 Hz, 1H);

Data shown in the carbon nuclear magnetic resonance spectrum of FIG. 2 was as follows: $^{13}$C-NMR (126 MHz, CDCl$_3$) δ 157.87 (t, J=32.1 Hz), 107.31 (t, J=313.9 Hz), 76.32, 74.09, 54.38;

Data shown in the fluorine nuclear magnetic resonance spectrum of FIG. 3 was as follows: $^{19}$F-NMR (471 MHz, CDCl$_3$) δ −61.16.

Example 2

In one embodiment, 87.5 grams of 2-bromo-2,2-difluoroacetic acid, 35 grams of 3-butyn-1-ol, 0.875 grams of p-toluenesulfonic acid and 600 grams of toluene were added into a reactor equipped with a thermometer, a reflux condenser, a water separator and a stirrer, and were subjected to a reaction at 100° C. until that no water was separated, and the reaction was carried out for 10 hours. After the reaction was completed, a distillation treatment was carried out to recover the solvent, then the remaining substances were subjected to a distillation under reduced pressure, and the fractions under the condition of 126-127° C./50 mmHg was collected, to obtain 110.2 grams of 3-butynyl 2-bromo-2,2-difluoroacetate with a yield of 97.1%, and a purity of 99.6%.

Example 3

In one embodiment, 87.5 grams of 2-bromo-2,2-difluoroacetic acid, 84 grams of 4-pentyn-1-ol, 1.5 grams of sulfuric acid, and 500 grams of toluene were added into a reactor equipped with a thermometer, a reflux condenser, a water separator and a stirrer, and were subjected to a reaction at 110° C. until that no water was separated, and the reaction was carried out for 10 hours. After the reaction was completed, a distillation treatment was carried out to recover the solvent and excess 4-pentyn-1-ol, then the remaining substances were subjected to a distillation under reduced pressure, and the fractions under the condition of 163-164° C./50 mmHg were collected, to obtain 114.5 grams of 4-pentynyl 2-bromo-2,2-difluoroacetate with a yield of 95.0%, and a purity of 99.6%.

Example 4

In one embodiment, 87.5 grams of 2-bromo-2,2-difluoroacetic acid, 98 grams of 5-hexyn-1-ol, 1.5 grams of sulfuric acid, 1.5 grams of phosphoric acid, and 500 grams of xylene were added into a reactor equipped with a thermometer, a reflux condenser, a water separator and a stirrer, and were subjected to a reaction at 120° C. until that no water was separated, and the reaction was carried out for 5 hours. After the reaction was completed, a distillation treatment was carried out to recover the solvent and excess 5-hexyn-1-ol, then the remaining substances were subjected to a distillation under reduced pressure and the fractions under the condition of 165-166° C./40 mmHg were collected, to obtain 123.5 grams of 5-hexynyl 2-bromo-2,2-difluoroacetate with a yield of 96.9%, and a purity of 99.8%.

Example 5

In one embodiment, 65.25 grams of 2-chloro-2,2-difluoroacetic acid, 140 grams of propargyl alcohol, 1.5 grams of sulfuric acid, 1.5 grams of p-toluenesulfonic acid, and 261 grams of cyclohexane were added into a reactor equipped with a thermometer, a reflux condenser, a water separator and a stirrer, and were subjected to a reaction at 60° C. until that no water was separated, and the reaction was carried out for 15 hours. After the reaction was completed, a distillation treatment was carried out to recover the solvent and excess propargyl alcohol, then the remaining substances were subjected to a distillation under reduced pressure, and the fractions under the condition of 110-111° C./50 mmHg were collected, to obtain 82.3 grams of propargyl 2-chloro-2,2-difluoroacetate with a yield of 97.6%, and a purity of 99.3%.

Figure 4:
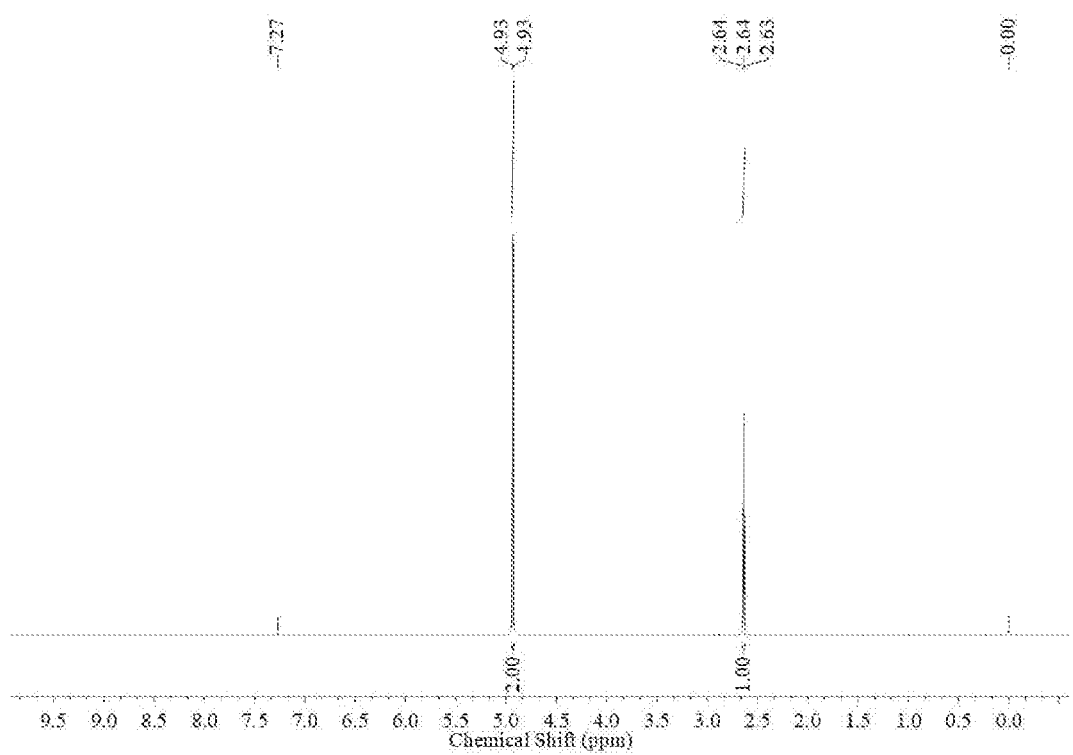
FIG. 4 illustrates a $^1$H-NMR spectrum of propargyl 2-chloro-2,2-difluoroacetate as prepared in Example 5.
Figure 5:
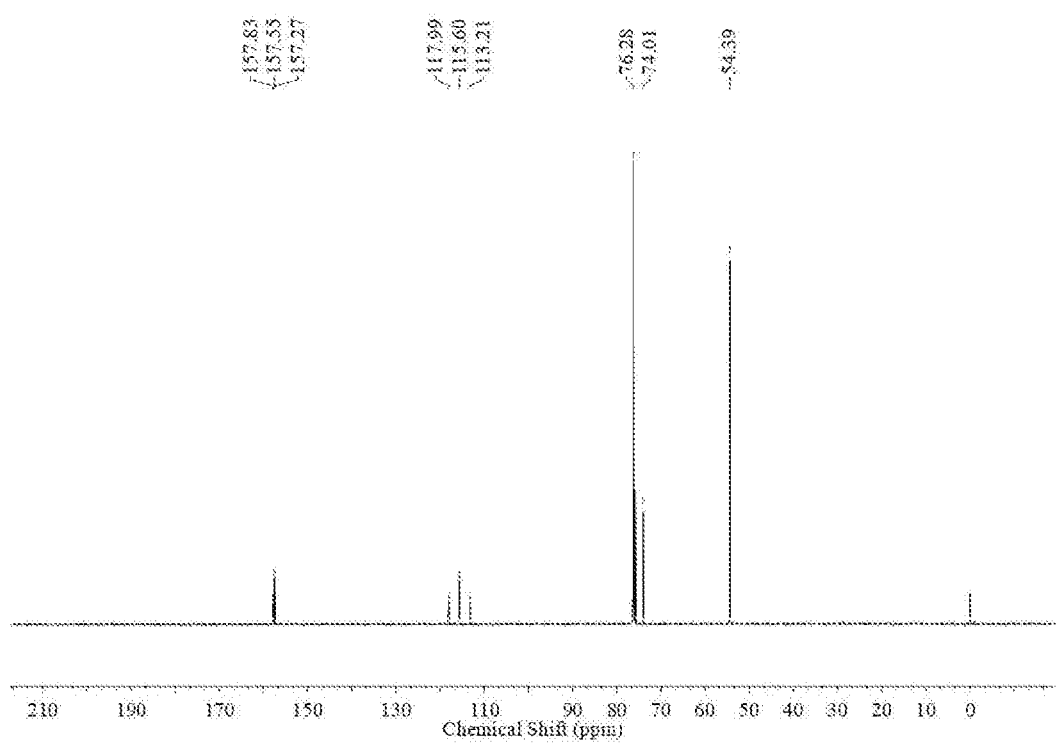
FIG. 5 illustrates a $^{13}$C-NMR spectrum of propargyl 2-chloro-2,2-difluoroacetate as prepared in Example 5.
Figure 6:
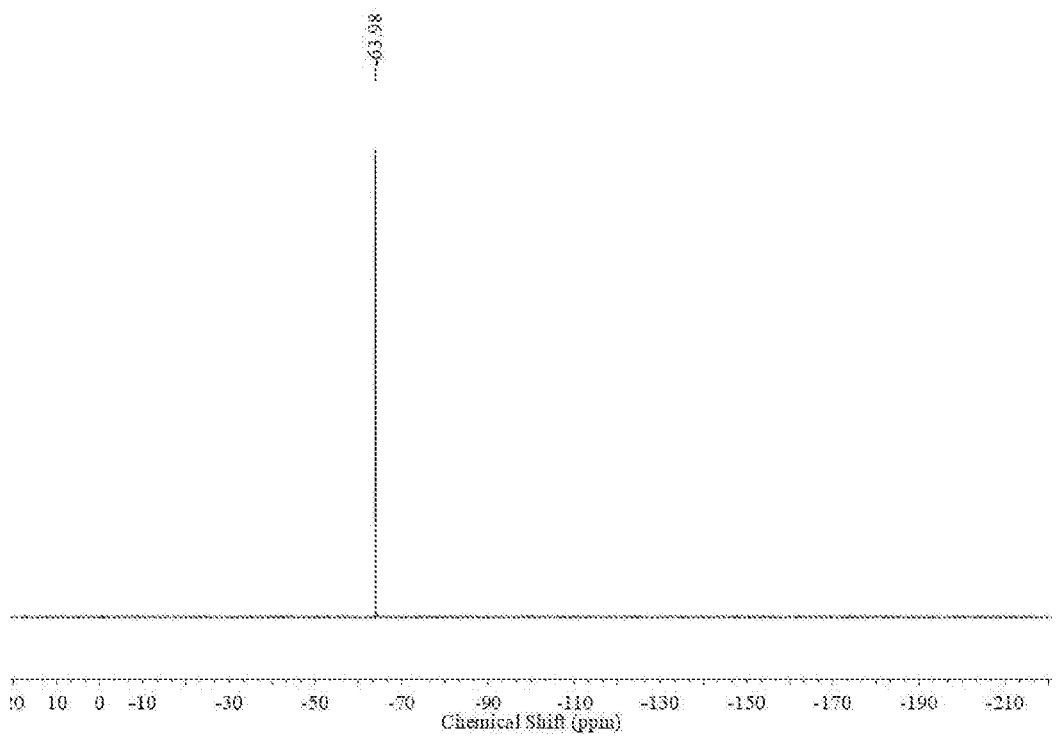
FIG. 6 illustrates a $^{19}$F-NMR spectrum of propargyl 2-chloro-2,2-difluoroacetate as prepared in Example 5.

Propargyl 2-chloro-2,2-difluoroacetate prepared in Example 5 was subjected to a nuclear magnetic resonance analysis. The results were shown in FIGS. 4-6, wherein FIG. 4 illustrates a hydrogen nuclear magnetic resonance spectrum, FIG. 5 illustrates a carbon nuclear magnetic resonance spectrum, and FIG. 6 illustrates a fluorine nuclear magnetic resonance spectrum. As can be seen from FIGS. 4-6, the structure of propargyl 2-chloro-2,2-difluoroacetate prepared in Example 5 of the present disclosure was confirmed by the nuclear magnetic analysis.

Data shown in the hydrogen nuclear magnetic resonance spectrum of FIG. 4 was as follows: $^1$H-NMR (500 MHz, CDCl$_3$) δ 4.93 (d, J=2.5 Hz, 2H), 2.64 (t, J=2.5 Hz, 1H); Data shown in the carbon nuclear magnetic resonance spectrum of FIG. 5 was as follows: $^{13}$C-NMR (126 MHz, CDCl$_3$) δ 157.55 (t, J=35.2 Hz), 115.60 (t, J=300.5 Hz), 76.28, 74.01, 54.39;
Data shown in the fluorine nuclear magnetic resonance spectrum of FIG. 6 was as follows: $^{19}$F-NMR (471 MHz, CDCl$_3$) δ −63.98.

Example 6

In one embodiment, 65.25 grams of 2-chloro-2,2-difluoroacetic acid, 35 grams of 3-butyn-1-ol, 1.5 grams of sulfuric acid, 1.5 grams of phosphoric acid, and 652.5 grams of toluene were added into a reactor equipped with a thermometer, a reflux condenser, a water separator and a stirrer, and were subjected to a reaction at 110° C. until that no water was separated, and the reaction was carried out for 10 hours. After the reaction was completed, a distillation treatment was carried out to recover the solvent, then the remaining substances were subjected to a distillation under reduced pressure, and the fractions under the condition of 124-125° C./50 mmHg were collected, to obtain 90.2 grams of 3-butynyl 2-chloro-2,2-difluoroacetate with a yield of 98.8%, and a purity of 99.6%.

Example 7

In one embodiment, 65.25 grams of 2-chloro-2,2-difluoroacetic acid, 84 grams of 4-pentyn-1-ol, 1.5 grams of sulfuric acid, and 500 grams of toluene were added into a reactor equipped with a thermometer, a reflux condenser, a water separator and a stirrer, and were subjected to a reaction at 110° C. until that no water was separated, and the reaction was carried out for 10 hours. After the reaction was completed, a distillation treatment was carried out to recover the solvent and excess 4-pentyn-1-ol, then the remaining substances were subjected to a distillation under reduced pressure, and the fractions under the condition of 157-158° C./50 mmHg were collected, to obtain 96.6 grams of 4-pentynyl 2-chloro-2,2-difluoroacetate with a yield of 98.3%, and a purity of 99.7%.

Example 8

In one embodiment, 65.25 grams of 2-chloro-2,2-difluoroacetic acid, 98 grams of 5-hexyn-1-ol, 1.5 grams of phosphoric acid, and 500 grams of xylene were added into a reactor equipped with a thermometer, a reflux condenser, a water separator and a stirrer, and were subjected to a reaction at 130° C. until that no water was separated, and the reaction was carried out for 5 hours. After the reaction was completed, a distillation treatment was carried out to recover the solvent and excess 5-hexyn-1-ol, then the remaining substances were subjected to a distillation under reduced pressure, and the fractions under the condition of 158-160° C./40 mmHg were collected, to obtain 103.3 grams of 5-hexynyl 2-chloro-2,2-difluoroacetate with a yield of 98.1%, and a purity of 99.4%.

The present disclosure provides a method for preparing alkynyl 2-halo-2,2-difluoroacetate. In some embodiments, the preparation method provided by the present disclosure could achieve a higher product yield and a higher product purity, with a yield of 95.0%-98.8% and a purity of 99.3%-99.8%.

The above are only the preferred embodiments of the present disclosure. Those ordinary skilled in the art will appreciate that other embodiments can be devised without departing from the scope as disclosed herein. Accordingly, the scope of the present disclosure is defined by the attached claims.

The invention claimed is:

1. A method of preparing an alkynyl 2-halo-2,2-difluoroacetate, comprising:
    subjecting a 2-halo-2,2-difluoro acetic acid, an alkynol, and a catalyst to an esterification reaction in a solvent, to obtain the alkynyl 2-halo-2,2-difluoroacetate,
    wherein the 2-halo-2,2-difluoro acetic acid is 2-bromo-2, 2-difluoroacetic acid or 2-chloro-2,2-difluoroacetic acid;

wherein when the 2-halo-2,2-difluoro acetic acid is 2-bromo-2,2-difluoroacetic acid, the esterification reaction is carried out at a temperature of 60-80° C. for 5-15 h; the catalyst is phosphoric acid; a mass ratio of the 2-halo-2,2-difluoro acetic acid to the catalyst is 1:0.08-0.1; and a molar ratio of the 2-halo-2,2-difluoro acetic acid to the alkynol is 1:4-5;

wherein when the 2-halo-2,2-difluoro acetic acid is 2-chloro-2,2-difluoroacetic acid, the esterification reaction is carried out at a temperature of 110-120° C. for 5-15 h; the catalyst is a combination of sulfuric acid and phosphoric acid; a mass ratio of the 2-halo-2,2-difluoro acetic acid to the catalyst is 1:0.02-0.05, and a molar ratio of the 2-halo-2,2-difluoro acetic acid to the alkynol is 1:1-4.

2. The method of claim 1, wherein the esterification reaction is carried out under a reflux condition, and during the esterification reaction, the water produced by the esterification reaction is continuously separated.

3. The method of claim 1, wherein the alkynol includes one or more of propargyl alcohol, 3-butyn-1-ol, 4-pentyn-1-ol and 5-hexyn-1-ol.

4. The method of claim 1, wherein the solvent includes one or more of cyclohexane, toluene and xylene.

5. The method of claim 1, wherein a mass ratio of the 2-halo-2,2-difluoro acetic acid to the solvent is 1:4-10.

* * * * *